United States Patent [19]
Tanner et al.

[11] Patent Number: 5,935,556
[45] Date of Patent: Aug. 10, 1999

[54] SUNSCREEN COMPOSITIONS

[75] Inventors: Paul Robert Tanner, Maineville; Christopher Irwin, Cincinnati, both of Ohio

[73] Assignee: The Procter & Gamble Company, Cincinnati, Ohio

[21] Appl. No.: 09/126,492

[22] Filed: Jul. 30, 1998

[51] Int. Cl.$^6$ .............................. A61K 7/42; A61K 7/44; A61K 7/00
[52] U.S. Cl. .............................. 424/59; 424/60; 424/400; 424/401
[58] Field of Search ................................ 424/59, 60, 400, 424/401

[56] References Cited
PUBLICATIONS

Rassat, F., et al., "Use of Sunscreens and Vitamins in the Daily–Use Cosmetic", DCI, pp. 16–30 (Dec. 1997).

Klein, K., "Encyclopedia of UV Absorbers for Sunscreen Products", Cosmetics & Toiletries, vol. 107, pp. 45–68 (Oct. 1992).

*Primary Examiner*—Shelley A. Dodson
*Attorney, Agent, or Firm*—Dara M. Kendall; Loretta J. Henderson; George W. Allen

[57] ABSTRACT

The present invention relates to compositions suitable for use as sunscreens which have improved storage stability and improved retention of UV absorbance capability. Methods of using the compositions are also disclosed. The compositions comprise an emulsion comprising a safe and effective amount of a UVA-absorbing dibenzoylmethane sunscreen active in one or more oil phases, a safe and effective amount of a formaldehyde donor preservative in one or more aqueous phases, and an emulsifier.

21 Claims, No Drawings

SUNSCREEN COMPOSITIONS

TECHNICAL FIELD

The present invention relates to compositions suitable for use as sunscreens which have excellent storage stability such that their UVA absorbance and microbial preservation capabilities are effectively maintained. The invention especially relates to emulsions containing an oil phase comprising a UVA-absorbing dibenzoylmethane sunscreen active and an aqueous phase comprising a formaldehyde donor preservative.

BACKGROUND OF THE INVENTION

It is well known that exposure to sunlight can pose a number of hazards to the skin. These damaging effects may result not only from sunbathing but also from the sunlight exposure associated with daily outdoor activities. The major short term hazard of prolonged exposure to sunlight is erythema, i.e. sunburn, which results from UVB radiation having a wavelength of from about 290 nm to about 320 nm. Over the long term, however, malignant changes in the skin surface often occur. Numerous epideminologic studies demonstrate a strong relationship between sunlight exposure and human skin cancer. Another long term hazard of ultraviolet radiation is premature aging of the skin, which is primarily caused by UVA radiation having a wavelength of from about 320 nm to about 400 nm. This condition is characterized by wrinkling and pigment changes of the skin, along with other physical changes such as cracking, telangiectasis, solar dermatoses, ecchymoses, and loss of elasticity. The adverse effects associated with exposure to UV radiation are more fully discussed in DeSimone, "Sunscreen and Suntan Products," *Handbook of Nonprescription Drugs,* 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation," *International Journal of Cosmetic Science,* 4, pp. 15–24 (1982); and U.S. Pat. No. 4,387,089, DePolo, issued Jun. 7, 1983.

As a result of the abovementioned hazards typically associated with sunlight exposure, the general public's interest in the sun protection product market has grown considerably. In today's commercial market, there are not only sunscreen products for sunbathing but there are also a variety of personal care products containing sunscreens, particularly cosmetic type products which are worn daily. "Personal care products" refer to health and cosmetic beauty aid products generally recognized as being formulated for beautifying and grooming the skin and hair. For example, personal care products include sunscreen products (e.g., lotions, skin creams, etc.), cosmetics, toiletries, and over-the-counter pharmaceutical products intended for topical usage.

A wide variety of sunscreen actives have been used in personal care products. It is desirable that the sunscreen active or active system provide broad spectrum UV protection, i.e., protection against both UVA radiation and UVB radiation. It is further desirable that the sunscreen actives are formulated to provide stable, efficacious, and aesthetically appealing sunscreen products. In addition, for economic reasons it is often desirable that the sunscreen actives be approved for global use. Dibenzoylmethane compounds are one class of sunscreen compounds which provide broad spectrum UV protection and are approved for global use.

In personal care products, sunscreen actives are often formulated with water, since the resulting systems tend to be more aesthetically appealing to the user. The presence of water, however, promotes the growth of microorganisms which can cause deterioration of the sunscreen product. This deterioration can undesirably alter a product, rendering it physically or chemically unaesthetic or shortening the product's useful life. In some instances, such deteriorated sunscreen products could even be injurious to humans. Therefore, sunscreen products are generally designed in an effort to minimize deterioration over the product's desired shelf life. Antimicrobial preservatives are typically included in aqueous sunscreen products to prolong their useful life during storage and usage and to maintain product efficacy (i.e., UV absorbance).

Antimicrobial preservatives should be non-irritating to the skin, effective against microorganisms typically found in aqueous sunscreen products which pose the greatest threat to the consumer, and/or which tend to cause sunscreen product instability (i.e., chemical side reactions and consequential product inefficacy), cost efficient, and easily formulated.

A wide variety of antimicrobial preservatives are commonly used in personal care products, including the parabens, isothizolinones, formaldehyde-donating preservatives such as hydantoins, alcohols, and others such as described in the Preservatives Documentary/Encyclopedia issue of *Cosmet. & Toilet.,* Vol. 102, No. 12 (1987). However, the formulation of aqueous systems containing dibenzoylmethane sunscreen actives is not straightforward. Formaldehyde donor preservatives, in particular, have been known to interact with dibenzoylmethanes. While not intending to be limited by theory, it is believed that an aldol reaction product is formed when dibenzoylmethanes are combined with formaldehyde-donating preservatives. Over time, this interaction tends to result in poor storage stability, i.e., increased microbial growth in the product and/or the loss of UV absorbance capability of the dibenzoylmethane sunscreen.

It has surprisingly been found that compositions which include an emulsion having at least one oil phase comprising a dibenzoylmethane sunscreen active and at least one aqueous phase comprising a formaldehyde-donating preservative exhibit excellent storage stability and retention of UV absorbance capability. The growth of microorganisms in the product and therefore spoilage of the product is effectively prevented, inhibited or retarded such that the product life is extended. It has also been found that these compositions provide a means of delivering the dibenzoylmethane sunscreen active to the skin in a non-irritating manner.

SUMMARY OF THE INVENTION

The present invention relates to a composition suitable for use as a sunscreen comprising an emulsion comprising a) at least one oil phase comprising a safe and effective amount of a UVA-absorbing dibenzoylmethane sunscreen active, b) at least one aqueous phase comprising water and a safe and effective amount of a formaldehyde donor preservative, and c) an emulsifier.

In another embodiment, the present invention is directed to a composition suitable for use as a sunscreen comprising an emulsion prepared by the process comprising:

a) combining an oil and a UVA-absorbing dibenzoylmethane sunscreen active to form an oily mixture;

b) separately combining water and a formaldehyde donor preservative to form an aqueous mixture; and c) combining the oily mixture(s), aqueous mixture(s) and an emulsifier to form an emulsion; wherein the composition comprises a safe and effective amount of the UVA-absorbing dibenzoylmethane sunscreen active and a safe and effective amount of the formaldehyde donor preservative.

The invention also relates to methods of using the compositions as a sunscreen.

DETAILED DESCRIPTION OF THE INVENTION

The compositions of the present invention are suitable for use as sunscreens and have excellent storage stability and retention of UV absorbance capability. The essential components of these compositions are described below. Also included is a nonexclusive description of various optional and preferred components useful in embodiments of the present invention.

The present invention can comprise, consist of, or consist essentially of any of the required or optional ingredients and/or limitations described herein. The present compositions can comprise, consist of, or consist essentially of the emulsion described herein.

All percentages and ratios are calculated on a weight basis unless otherwise indicated. All percentages are calculated based upon the total composition unless otherwise indicated.

All molar weights are weight average molecular weights and are given in units of grams per mole.

All ingredient levels are exclusive of solvents, by-products, or other impurities that may be present in commercially available sources, unless otherwise indicated.

All measurements made are at ambient room temperature, which is approximately 73° F., unless otherwise designated.

All documents referred to herein, including patents, patent applications, and printed publications, are hereby incorporated by reference in their entirety in this disclosure.

By "safe and effective amount" is meant an amount of a compound, component, or composition (as applicable) sufficient to significantly induce a positive effect (e.g., photoprotection or stability), but low enough to avoid serious side effects, (e.g., undue toxicity or allergic reaction), i.e., to provide a reasonable benefit to risk ratio, within the scope of sound medical judgment.

Emulsion

The compositions of the present invention comprise an emulsion having at least one oil phase comprising an oil and a UVA-absorbing dibenzoylmethane sunscreen active, at least one aqueous phase comprising water and a formaldehyde donor preservative, and one or more emulsifiers. The emulsion typically comprises from about 1% to about 75% total oil phase and from about 25% to about 99 % total aqueous phase.

In emulsion technology, the term "dispersed phase" means that the phase exists as small particles or droplets that are suspended in and surrounded by a continuous phase. In the compositions of the invention, an oil phase may be dispersed in a continuous water phase, or the water phase may be dispersed in a continuous oil phase. Preferred compositions hereof comprise an oil phase dispersed in a continuous water phase. The emulsions of the present compositions can be formulated in a number of ways, including, but not limited to, oil-in-water, water-in-oil, water-in-oil-in-water, and oil-in-water-in-silicone emulsions. Preferred emulsions are oil-in-water emulsions. The emulsions can have a broad range of viscosities, e.g., from about 1 cps to about 1,000,000 cps.

The oil phase comprises one or more oils and the oil-soluble components of the present composition, including at least one dibenzoylmethane sunscreen active. The emulsions typically comprise from about 0.1% to about 50% oil.

Suitable oils may be derived from animals, plants, or petroleum and may be natural or synthetic (i.e. man-made). Preferred oils are substantially water-insoluble, more preferably essentially water-insoluble. Suitable oils include, but are not limited to, mineral oil; petrolatum; straight and branched chain hydrocarbons having from about 7 to about 40 carbon atoms; $C_1$–$C_{30}$ alcohol esters of $C_1$–$C_{30}$ carboxylic acids and $C_2$–$C_{30}$ dicarboxylic acids; mono-, di-, and triglycerides of $C_1$–$C_{30}$ carboxylic acids; alkylene glycol esters of $C_1$–$C_{30}$ carboxylic acids; propoxylated and ethoxylated derivatives of the aforementioned materials; $C_1$–$C_{30}$ mono- and polyesters of sugars and related materials; fatty alcohols, ethers, organopolysiloxane oils; vegetable oils and hydrogenated vegetable oils; animal fats and oils; and mixtures thereof. Examples of suitable oils are described in U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; and U.S. Pat. No. 5,069,897, to Orr, issued Dec. 3, 1991. Preferred oils include $C_{12}$–$_{15}$ alkyl benzoate, cetyl palmitate, isodecyl neopentanoate, isononyl isonanoate, isopropyl myristate, isopropyl palmitate, isostearyl isostearate, cholesterol, octyldecanol, octyldodecanol, PPG-14 butyl ether, PPG-11 stearyl ether, hydrogenated polyisobutene, isoeicosane, isohexadecane, polydecene, cetyl dimethicone, cyclomethicone, dimethicone, dimethicone copolyol, dimethiconol, phenyl trimethicone, and lanolin.

The dibenzoylmethane sunscreen active provides protection against UV radiation of wavelengths between about 320 nm to about 400 nm (i.e., the active provides both UVA and UVB protection). Examples of such dibenzoylmethane sunscreen actives are described in U.S. Pat. No. 4,489,057, issued to Welters et al. on Dec. 18, 1984; U.S. Pat. No. 4,387,089, issued to Depolo on Jun. 7, 1983; and in *Sunscreens: Development, Evaluation, and Regulatory Aspects,* edited by N. J. Lowe and N. A. Shaath, Marcel Dekker, Inc. (1990).

Suitable dibenzoylmethane sunscreen actives include, but are not limited to, those selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1, 1 -dimethylethyl)-4'methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'tert-butyl-4'methoxydibenzoylmethane, and mixtures thereof. Preferred dibenzoylmethane sunscreen actives include those selected from the group consisting of 4-(1,1-dimethylethyl)-4'methoxydibenzoylmethane, isopropyldibenzoylmethane, and mixtures thereof. 4-(1,1-dimethylethyl)-4'methoxydibenzoylmethane is more preferred.

The sunscreen active, 4-(1,1-dimethylethyl)-4'methoxydibenzoylmethane, which is also known as butyl methoxydibenzoylmethane or Avobenzone, is commercially available under the names Parsol® 1789 from Givaudan-Roure (International) S.A. (Basel, Switzerland) and Euso-lex® 9020 from Merck & Co., Inc. (Whitehouse Station, N.J.). The sunscreen 4-isopropyldibenzoylmethane, which is also known as isopropyl dibenzoylmethane, is commercially available from Merck under the name Eusolex® 8020.

The dibenzoylmethane sunscreen active is present in a safe and effective amount to provide broad spectrum UV protection either independently or in combination with other UV protective actives which may be present in the composition, preferably in a total amount of from about 0.1% to about 10%, more preferably from about 0.2% to about 7%, and most preferably from about 0.4% to about 5%. Exact amounts of the dibenzoylmethane sunscreen active will vary depending upon the desired Sun Protection Factor, i.e. the "SPF" of the composition and the desired level of UVA protection. (SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See Federal Register, 43, No. 166, pp. 38206–38269, Aug. 25, 1978).

The dibenzoylmethane sunscreen active is substantially in at least one oil phase; e.g., at least about 50%, preferably at least about 75% of the dibenzoylmethane sunscreen active is in one or more oil phases.

The aqueous phase comprises water and the water-soluble components of the present composition, including one or more formaldehyde donor preservatives. Typically, the emulsion comprises from about 20% to about 98% water.

The formaldehyde donor preservative is an antimicrobial preservative, i.e., a compound or substance that kills microorganisms or prevents, inhibits or retards their growth and reproduction. For purposes of the present invention, formaldehyde donor preservatives include formaldehyde itself and any other antimicrobial preservatives that either form or release formaldehyde into a composition. Preferred preservatives are formed by binding formaldehyde to a heterocyclic organic compound from which the formaldehyde is then released slowly over time. Formaldehyde-donating preservatives are described in U.S. Pat. No. 5,681,852, issued to Bissett on Oct. 28, 1997 and U.S. Pat. No. 5,037,843, issued to Schoenberg on Aug. 6, 1991.

Preferred formaldehyde donor preservatives are DMDM Hydantoin (1,3-dimethylol-5,5-dimethyl hydantoin), DM Hydantoin (5,5-dimethyl hydantoin), and mixtures thereof. DMDM Hydantoin and DM Hydantoin are commercially available from Lonza, Inc. (Basel, Switzerland) under the names Glydant and Dantoin DMH, respectively. DMDM Hydantoin is more preferred.

The formaldehyde donor preservative is used in a safe and effective antimicrobial amount, preferably from about 0.01% to about 1%, more preferably from about 0.02% to about 0.5%, and most preferably from about 0.05% to about 0.3%, by weight of the composition. The formaldehyde donor preservative is substantially in at least one aqueous phase; e.g., at least about 50%, preferably at least about 75% of the preservative is present in one or more aqueous phases.

One or more emulsifiers are employed in an amount effective to stabilize the emulsion. Suitable emulsifiers include a wide variety of nonionic, cationic, anionic, and zwitterionic emulsifiers. See McCutcheon's, Detergents and Emulsifiers, North American Edition (1986), published by Allured Publishing Corporation; U.S. Pat. No. 5,011,681 issued to Ciotti et al. on Apr. 30, 1991; U.S. Pat. No. 4,421,769 issued to Dixon et al. on Dec. 20, 1983; and U.S. Pat. No. 3,755,560 issued to Dickert et al. on Aug. 28, 1973.

Suitable emulsifier types include, but are not limited to, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers include, but are not limited to, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. Preferred emulsifiers are steareth-2, steareth-21, TEA stearate, diethanolamine cetyl phosphate, potassium cetyl phosphate, and mixtures thereof. The emulsifier can be used individually or as a mixture of two or more and comprise from about 0.1% to about 10%, more preferably from about 0.15% to about 7%, and most preferably from about 0.25% to about 5% of the compositions of the present invention.

The emulsions and compositions of the present invention can be formulated into a wide variety of product types, including creams, lotions, milks, sticks, mousses, gels, oils, tonics, and sprays. Preferred compositions are formulated into lotions, creams, gels and sprays. These product forms may be used for a number of applications, including, but not limited to, hand and body lotions, cold creams, facial moisturizers, anti-acne preparations, topical analgesics, make-ups including foundations and lipsticks, and the like. Any additional components required to formulate such products vary with product type and can be routinely chosen by one skilled in the art.

If emulsions or compositions of the present invention are formulated as an aerosol and applied to the skin as a spray-on product, a propellant is preferably added to the composition. Examples of suitable propellants include chlorofluorinated lower molecular weight hydrocarbons. A more complete, nonlimiting disclosure of propellants useful herein can be found in Sagarin, Cosmetics Science and Technology, 2nd Edition, Vol. 2, pp. 443–465 (1972).

Optional Components

The compositions of the present invention may contain a variety of other ingredients such as are conventionally used in a given product type provided that they do not unacceptably alter the benefits of the invention. These optional components should be suitable for application to human skin, that is, when incorporated into the composition they are suitable for use in contact with human skin without undue toxicity, incompatibility, instability, allergic response, and the like, within the scope of sound medical or formulator's judgment. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, additional antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skinbleaching agents (or lightening agents) (e.g., hydroquinone, kojic acid, ascorbic acid, magnesium ascorbyl phosphate, ascorbyl glucosamine), skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, including agents for preventing, retarding, arresting, and/or reversing skin wrinkles (e.g., alpha-hydroxy acids such as lactic acid and glycolic acid and beta-hydroxy acids such as salicylic acid), thickeners, and vitamins and derivatives thereof (e.g. tocopherol, tocopherol acetate, beta carotene, retinoic acid, retinol, retinoids, retinyl palmitate, niacin, niacinamide, and the like). The compositions may contain carrier components such as are known in the art. Such carriers can include one or more compatible liquid or solid filler diluents or vehicles which are suitable for application to human skin.

The compositions may contain one or more of such optional components. Preferred compositions optionally contain one or more materials selected from UVB sunscreen actives, anti-acne actives, artificial tanning agents, humectants, moisturizers, skin conditioners, and thickening/structuring agents.

a) UVB Sunscreen Actives

Preferred compositions of the present invention optionally comprise a UVB sunscreen active, which absorbs UV radiation having a wavelength of from about 290 nm to about 320 nm. As used herein, an optional UVB sunscreen active means an active other than the dibenzoylmethane sunscreen active, which may itself possess UVB absorption properties. Such compositions comprise an amount of the UVB active effective to provide protection against UVB radiation independently or in combination with other UV protective actives which may be present in the compositions, preferably from about 0.5% to about 20% of a UVB sunscreen active. Exact amounts of UVB sunscreen actives will vary depending upon the sunscreen chosen and the desired SPF of the product.

A wide variety of UVB sunscreen actives are useful herein. Nonlimiting examples of these sunscreen actives are described in U.S. Pat. No. 5,087,445, to Haffey et al., issued Feb. 11, 1992; and U.S. Pat. Nos. 5,073,371 and 5,073,372, to Turner et al., issued Dec. 17, 1991. Preferred UVB sunscreen actives are selected from the group consisting of octyl methoxycinnamate, octocrylene, 4-methylbenzylidene camphor, 2-phenyl-benzimidazole-5-sulfonic acid, octyl salicylate, zinc oxide, titanium dioxide, iron oxide, and mixtures thereof. More preferred UVB sunscreen actives are those selected from the group consisting of octyl methoxycinnamate, octocrylene, 2-phenyl-benzimidazole-5-sulfonic acid, zinc oxide, and mixtures thereof. Salt and acid-neutralized forms of the acidic sunscreens are also useful herein.

b) Anti-Acne Actives

The compositions of the present invention may comprise one or more anti-acne actives. Examples of useful anti-acne actives are described in further detail in U.S. Pat. No. 5,607,980, issued to McAtee et al., on Mar. 4, 1997.

c) Artificial Tanning Agents

The compositions of the present invention can optionally comprise one or more artificial tanning agents. Suitable tanning agents include dihydroxyacetone, tyrosine, and tyrosine esters. See

*The Merck Index*, Tenth Edition, entry 3167, p. 463 (1983), and "Dihydroxyacetone for Cosmetics", E. Merck Technical Bulletin, 03–304 110, 319 897, 180 588.

d) Structuring Agent

The compositions of the present invention may contain a structuring agent. Structuring agents are particularly preferred in the oil-in-water emulsions of the present invention. Without being limited by theory, it is believed that the structuring agent assists in providing theological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 0.5% to about 20%, more preferably from about 1% to about 10%, most preferably from about 1% to about 5%, of one or more structuring agents.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-2 1), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, steareth-21, and mixtures thereof.

e) Thickening Agent (including thickeners and gelling agents)

The compositions of the present invention can comprise one or more thickening agents, preferably from about 0.1% to about 5%, more preferably from about 0.1% to about 3%, and most preferably from about 0.25% to about 2%, by weight of the composition. Nonlimiting classes of thickening agents include those selected from the group consisting of:

(i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; and in *CTFA International Cosmetic Ingredient Dictionary*, Fourth edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $Cl_4$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from the group consisting of carbomers, acrylates/$C_{10}$–$C_{30}$ alkyl acrylate crosspolymers, and mixtures thereof.

(ii) Crosslinked Polyacrylate Polymers

The compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987.

(iii) Polyacrylamide Polymers

The compositions of the present invention can optionally comprise polyacrylamide polymers, especially nonionic polyacrylamide polymers including substituted branched or unbranched polymers. Most preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

(iv) Polysaccharides

A wide variety of polysaccharides are useful herein. "Polysaccharides" refer to gelling agents which contain a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans comprising a linear chain of (1–3) linked glucose units with a (1–6) linked glucose every three units, a commercially available example of which is Clearogel™ CS11 from Michel Mercier Products Inc. (Mountainside, N.J.).

(v) Gums

Other thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, camitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Preferred compositions of the present invention include a thickening agent selected from the group consisting of carboxylic acid polymers, crosslinked polyacrylate polymers, polyacrylamide polymers, and mixtures thereof, more preferably selected from the group consisting of carboxylic acid polymers, polyacrylamide polymers, and mixtures thereof.

f) Humectants, Moisturizers, and Skin Conditioners

Preferred compositions optionally comprise one or more humectants, moisturizers, or skin conditioners. A variety of these materials can be employed and each can be present at a level of from about 0.01% to about 20%, more preferably from about 0.1% to about 10%, and most preferably from about 0.5% to about 7%. These materials include, but are not limited to, guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, to Orr et al., issued Dec. 11, 1990.

Also useful are various $C_1$–$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,305, 514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Methods For Protecting The Skin From UV Radiation

The compositions of the present invention are suitable for use as a sunscreen to provide protection to human skin from the harmful effects of UV radiation which include, but are not limited to sunburn and premature aging of the skin. The present invention therefore also relates to methods of protecting human skin from the harmful effects of UV radiation, including attenuating or reducing the amount of UV radiation which reaches the skin's surface.

To protect the skin, a safe and effective (photoprotective) amount of the composition is topically applied to the skin. "Topical application" refers to application of the present compositions by spreading, spraying, etc. onto the surface of the skin. The exact amount applied may vary depending on the level of UV protection desired. From about 0.5 mg of composition per cm$^2$ of skin to about 25 mg of composition per cm$^2$ of skin are typically applied.

EXAMPLES

The following examples further describe and demonstrate embodiments within the scope of the present invention. The examples are given solely for the purpose of illustration and are not to be construed as limitations on the present invention, as many variations thereof are possible without departing from the spirit and scope of the invention.

The following sunscreen products are representative of the present invention.

|  | Wt % | |
| --- | --- | --- |
| Component | Example I | Example II |
| Premix 1 | | |
| Water | 75.05 | 61.55 |
| Glycerin | 3 | 3 |
| Disodium EDTA | 0.1 | 0.1 |
| Premix 2 | | |
| Water | 3 | 3 |
| Glycerin | 3 | 3 |
| DMDM Hydantoin/Iodopropyl Butylcarbamate Mixture | 0.2 | 0.2 |
| Premix 3 | | |
| Steareth-2 | 0.15 | 0.15 |
| Steareth-21 | 1.35 | 1.35 |
| Cetyl Alcohol | 1 | 1 |
| Stearyl Alcohol | 1 | 1 |
| Behenyl Alcohol | 1 | 1 |
| $C_{12-15}$ Alcohols Benzoate | 8 | 18 |
| Octocrylene | 0.75 | 2.25 |
| Avobenzone | 1 | 3 |
| Sepigel 305 | 1.4 | 1.4 |

[1] Commercially available from Lonza, Inc. under the tradename Glydant Plus

Mix the components of Premix 1 in a suitable vessel. Separately, combine the following components of Premix 3 in a suitable container: Steareth-2, Steareth-21, cetyl alcohol, stearyl alcohol, behenyl alcohol, $C_{12-15}$ alcohols benzoate, Octocrylene, and Avobenzone. Heat both premixes separately to about 75° C. under mixing. Slowly, add Premix 3 to Premix 1 under agitation while milling. Cool to about 60° C. and then add the Sepigel 305. Continue milling until the mixture reaches 55° C. and then cool further with mixing. Mix the components of Premix 2 and heat to 45° C. Once the main batch cools to 45° C., add Premix 2 and continue to cool while mixing. Further cool batch mixture to about to 30° C. under agitation and pour into suitable storage containers.

What is claimed is:

1. A composition suitable for use as a sunscreen comprising an emulsion comprising:
    a) at least one oil phase comprising an oil and a UVA-absorbing dibenzoylmethane sunscreen active;
    b) at least one aqueous phase comprising water and a formaldehyde donor preservative; and
    c) an emulsifier;
wherein the composition comprises, based on the weight of the composition, a safe and effective amount of the UVA-absorbing dibenzoylmethane sunscreen and a safe and effective amount of the formaldehyde donor preservative.

2. The composition of claim 1 wherein the composition comprises, by weight of the composition, from about 0.1% to about 10% of the dibenzoylmethane sunscreen active and from about 0.01% to about 1% of the formaldehyde donor preservative.

3. The composition of claim 1 wherein the composition comprises, by weight of the composition, from about 0.2% to about 7% of the dibenzoylmethane sunscreen active and from about 0.02% to about 0.5% of the formaldehyde donor preservative.

4. The composition of claim 1 wherein the composition comprises, by weight of the composition, from about 0.4% to about 5% of the dibenzoylmethane sunscreen active and from about 0.05% to about 0.3% of the formaldehyde donor preservative.

5. The composition of claim 1 wherein the dibenzoylmethane sunscreen active is selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'tert-butyl-4'methoxydibenzoylmethane, and mixtures thereof.

6. The composition of claim 1 wherein the dibenzoylmethane sunscreen active is selected from the group consisting of 4-isopropyldibenzoylmethane, 4-(1,1-dimethylethyl)-4'methoxydibenzoylmethane, and mixtures thereof.

7. The composition of claim 1 wherein the formaldehyde donor preservative is selected from the group consisting of DMDM hydantoin, DM hydantoin, and mixtures thereof.

8. The composition of claim 1 wherein the formaldehyde donor preservative is DMDM hydantoin.

9. The composition of claim 1 wherein the composition further comprises a safe and effective amount of a UVB sunscreen active.

10. The composition of claim 9 wherein the composition comprises from about 0.5% to about 20%, by weight of the composition, of the UVB sunscreen active.

11. The composition of claim 10 wherein the UVB sunscreen active is selected from the group consisting of octyl methoxycinnamate, octocrylene, 4-methylbenzylidene camphor, 2-phenyl-benzimidazole-5-sulfonic acid, octyl salicylate, zinc oxide, titanium dioxide, iron oxide, and mixtures thereof.

12. The composition of claim 11 wherein the UVB sunscreen active is selected from the group consisting of octyl methoxycinnamate, octocrylene, 2-phenyl-benzimidazole-5-sulfonic acid, zinc oxide, and mixtures thereof.

13. The composition of claim 1 wherein at least about 75% of the total amount of dibenzoylmethane sunscreen active in the composition is in one or more of the oil phases and at least about 75% of the formaldehyde donor preservative is in one or more of the aqueous phases.

14. The composition of claim 5 wherein the formaldehyde donor preservative is selected from the group consisting of DMDM hydantoin, DM hydantoin, and mixtures thereof.

15. The composition of claim 14 wherein the composition further comprises from about 0.5% to about 20%, by weight of the composition, of a UVB sunscreen active.

16. The composition of claim 15 wherein the UVB sunscreen active is selected from the group consisting of octyl methoxycinnamate, octocrylene, 4-methylbenzylidene camphor, 2-phenyl-benzimidazole-5-sulfonic acid, octyl salicylate, zinc oxide, titanium dioxide, iron oxide, and mixtures thereof.

17. The composition of claim 16 wherein the UVB sunscreen active is selected from the group consisting of octyl methoxycinnamate, octocrylene, 2-phenyl-benzimidazole-5-sulfonic acid, zinc oxide, and mixtures thereof.

18. The composition of claim 8 wherein the composition further comprises from about 0.5% to about 20%, by weight of the composition, of a UVB sunscreen active.

19. The composition of claim 18 wherein the UVB sunscreen active is selected from the group consisting of octyl methoxycinnamate, octocrylene, 4-methylbenzylidene camphor, 2-phenyl-benzimidazole-5-sulfonic acid, octyl salicylate, zinc oxide, titanium dioxide, iron oxide, and mixtures thereof.

20. The composition of claim 19 wherein the UVB sunscreen active is selected from the group consisting of octyl methoxycinnamate, octocrylene, 2-phenyl-benzimidazole-5-sulfonic acid, zinc oxide, and mixtures thereof.

21. A composition suitable for use as a sunscreen comprising an emulsion prepared by the process comprising:
 a) combining an oil and a UVA-absorbing dibenzoylmethane sunscreen active to form an oily mixture;
 b) separately combining water and a formaldehyde donor preservative to form an aqueous mixture; and
 c) combining the oily mixture, the aqueous mixture and an emulsifier to form an emulsion;
wherein the composition comprises, based on the weight of the composition, a safe and effective amount of the UVA-absorbing dibenzoylmethane sunscreen active and a safe and effective amount of the formaldehyde donor preservative.

* * * * *